United States Patent [19]
Wijay

[11] Patent Number: 5,643,278
[45] Date of Patent: Jul. 1, 1997

[54] STENT DELIVERY SYSTEM

[75] Inventor: Bandula Wijay, Houston, Tex.

[73] Assignee: Leocor, Inc., Houston, Tex.

[21] Appl. No.: 418,087

[22] Filed: Apr. 6, 1995

[51] Int. Cl.[6] .................................................. A61M 29/00
[52] U.S. Cl. ........................ 606/108; 606/194; 606/198
[58] Field of Search ............................... 606/192, 194, 606/195, 198, 108; 623/1, 12; 604/282

[56] References Cited

U.S. PATENT DOCUMENTS

| Re. 34,037 | 8/1992 | Inoue et al. . | |
|---|---|---|---|
| 4,503,569 | 3/1985 | Dotter . | |
| 4,732,152 | 3/1988 | Wallsten et al. . | |
| 4,740,207 | 4/1988 | Kreamer . | |
| 4,795,458 | 1/1989 | Regan . | |
| 4,798,586 | 1/1989 | Stevens | 606/194 |
| 4,913,141 | 4/1990 | Hillstead . | |
| 4,950,227 | 8/1990 | Savin et al. | 606/192 |
| 4,964,853 | 10/1990 | Sugiyama et al. . | |
| 4,990,151 | 2/1991 | Wallsten . | |
| 5,069,674 | 12/1991 | Fearnot et al. | 604/282 |
| 5,100,429 | 3/1992 | Sinofsky et al. | 606/195 |
| 5,108,416 | 4/1992 | Ryan et al. . | |
| 5,135,536 | 8/1992 | Hillstead . | |
| 5,158,548 | 10/1992 | Lau et al. . | |
| 5,160,341 | 11/1992 | Brenneman et al. . | |
| 5,163,951 | 11/1992 | Pinchuk et al. . | |
| 5,163,952 | 11/1992 | Froix . | |
| 5,163,958 | 11/1992 | Pinchuk . | |
| 5,197,978 | 3/1993 | Hess | 606/194 |
| 5,234,457 | 8/1993 | Andersen | 606/198 |
| 5,282,823 | 2/1994 | Schwartz et al. . | |
| 5,282,824 | 2/1994 | Gianturco . | |
| 5,480,423 | 1/1996 | Ravenscroft et al. | 623/1 |

*Primary Examiner*—Michael Buiz
*Assistant Examiner*—Patrick W. Rasche
*Attorney, Agent, or Firm*—Rosenblatt & Redano P.C.

[57] ABSTRACT

A catheter assembly for the delivery of a vascular stent into human arteries and veins is disclosed. The system disclosed in the present invention is an apparatus capable of deploying a vascular stent mounted on a catheter, either on a balloon catheter or on the distal portion of a catheter tube. In the case of a stent mounted on the balloon of a balloon catheter, the spring sheath is withdrawn and the balloon is inflated to deploy the stent to the inner wall of the vasculature. In the case of a self-expanding stent, the spring sheath is withdrawn, causing the stent to expand to the vessel wall. The apparatus is withdrawn after the stent has been deployed.

23 Claims, 3 Drawing Sheets

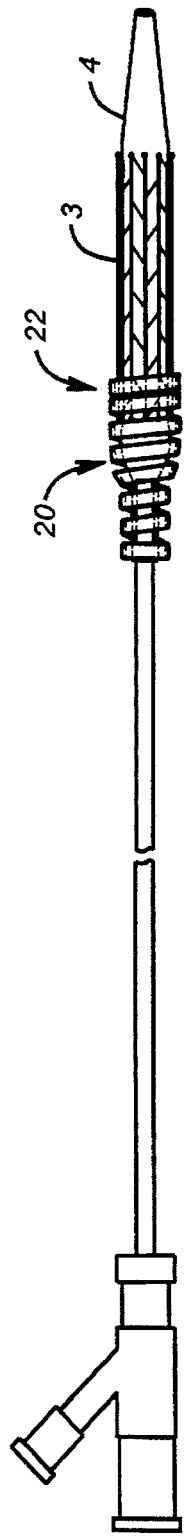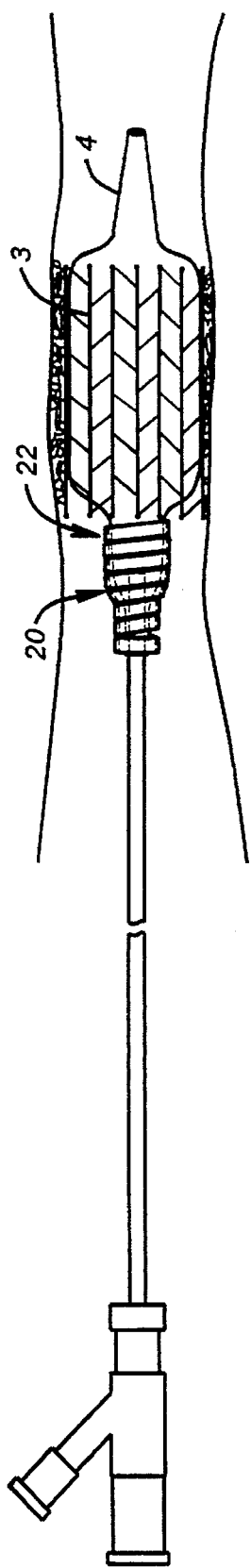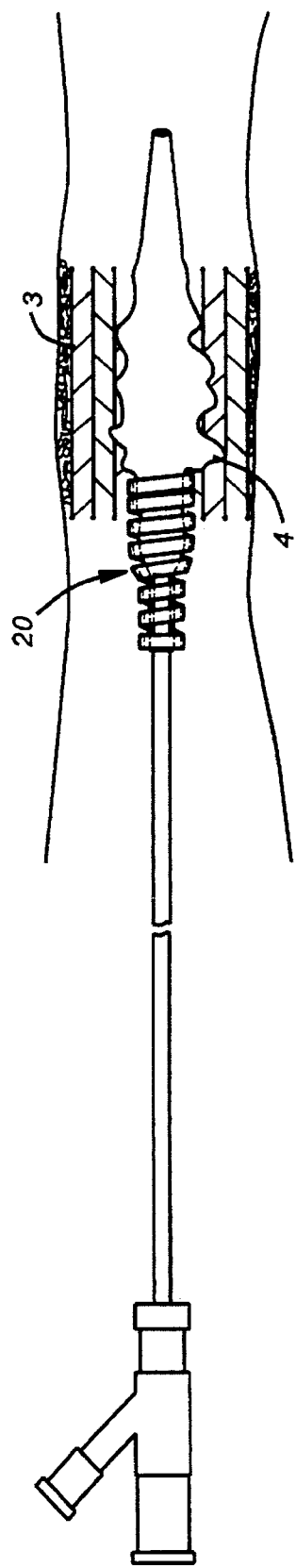

STENT DELIVERY SYSTEM

FIELD OF THE INVENTION

The field of the invention relates to vascular stenting. Stents are used to maintain patency of vessels in the body that have been dilated by other means such as balloon angioplasty and/or mechanical atheractomy.

BACKGROUND OF THE INVENTION

Stenotic lesions in human arteries are dilated using balloon catheters. A balloon catheter typically consists of a long, elongated tube having a strong elongated balloon member attached to its distal end. The balloon in most cases can be inflated independently so that the lesion is compressed so as to open the stenotic lesion. This procedure is called angioplasty. Balloon catheters are made in balloons having different diameters, for example, 2.0 mm to 10.0 mm in diameter. Angioplasty is performed in both coronary arteries, i.e., arteries supplying blood to the heart muscle, as well as in other arteries of the body. When angioplasty is performed in coronary arteries, it is called PTCA—percutaneous transluminal coronary angioplasty—and when performed on other vessels, it is called PTA—percutaneous transluminal angioplasty.

In either case, after balloon angioplasty, the vessel may reclose due to many factors. The early or acute reclosure or late or restenosis is one of the most important limitations of balloon angioplasty. At present, devices called "stents" are placed after or during balloon angioplasty to maintain the patency of the vessel. Stents are metallic or nonmetallic structures that are placed in the artery at the lesion location to maintain the patency. Several stents have been developed and are described in the literature. U.S. Pat. No. 4,649,922 by Wiktor; U.S. Pat. No. 4,733,665 and U.S. Pat. No. 4,739,762 by Palmaz, et al.; U.S. Pat. No. 4,800,882 by Gianturco, et al.; U.S. Pat. No. 4,954,126 by Wallstein, et at., describe a few of the stents that have been developed for the purpose of stenting the vascular lesion to maintain patency post-balloon angioplasty or mechanical atheractomy.

The outcome of vascular stenting is under several clinical studies, both in the U.S. and in Europe. One of the main complications is the delivery of the stent to the lesion location. In the United States, stents such as the Palmaz-Schatz stent by Johnson & Johnson International Systems (JJIS) is sold mounted on a delivery catheter. Similarly, the Gianturco-Roubin stent made by Cook Inc. is also sold mounted on a delivery catheter. In either case, the delivery catheter is a balloon catheter, similar to a normal PTCA or PTA balloon catheter. The metallic stent, the Palmaz-Schatz or the Gianturco-Roubin stent, is mounted on the folded balloon by sliding the stent onto it. The stent is held in place by a polymer sheath that extends the entire length of the catheter body. In Europe, the stent is sold separately. When the physician decides to place a stent in the dilated stenotic lesion, he mounts the stent on the folded balloon so as to deploy it at the lesion.

It is known in the literature that often the unprotected stent has a tendency to slide off the balloon portion of the catheter which can result in losing the stent inside the arteries of the body. It is, therefore, quite important that the stent is properly secured to the stent delivery system, be it a balloon catheter or another system for safe delivery and deployment of the stent. For this reason, the stent sold by JJIS is mounted on a balloon catheter and the stent is secured in place by a sheath. The sheath is placed substantially over the entire length of the stent and proximally the sheath extends toward the proximal end of the balloon catheter. Often, the sheath proximally is attached to a "Y" adapter. The entire sheath assembly can be slid over the balloon catheter and moved back and forth. By retracting the sheath, the stent can be exposed for deployment.

In a typical procedure, the physician performs balloon angioplasty on a stenotic lesion. The primary catheter used for dilation of the lesion is then with-drawn using an extension guidewire. The catheter (balloon-mounted stent delivery catheter) is then threaded to the lesion location so that the stent is at the location as determined by fluoroscopic X-ray. The sheath is then slid back sufficiently to expose the stent. The balloon is then inflated to deploy the stent and the balloon is subsequently deflated and the entire apparatus is withdrawn, leaving a guidewire in place. A third catheter having a high-pressure balloon is then threaded beneath the stent and is inflated to higher pressure (16–22 atmospheres) to seat and embed the stent into the intimal wall of the artery.

Several devices have been developed and invented to deliver stents. One such developed by JJIS was earlier discussed. This system has the disadvantage that the delivery catheter and the accompanying sheath have a very large diameter and are relatively stiff in the area near the stent. When the distal 20–30 cm of the catheter is stiff, it makes it very difficult and often impossible for the catheter to track the guidewire to tortuous vessels in the body. This often limits the use of stents to proximal lesions of the coronary arteries. Secondly, due to the fact that the sheath makes the profile of the catheter quite large (0.050–0.070" in some cases), it is often difficult to cross even those lesions that have been previously dilated.

Other devices have been invented for the delivery of stents. Such a device is described in U.S. Pat. No. 5,108,416 by Ryan and Chiev. This concept appears to resolve the problem of a stent sliding off the balloon by the use of holding cups, resulting in a stent delivery catheter having two (or one) bulky structures on the balloon at the location of the stent.

In order for a catheter to track well into the tortuous vasculature, it is quite important that the apparatus is quite flexible and it has neolithic bending characteristics. This means that the catheter body should not have areas that are bulky so that when the catheter is bent into different planes three dimensionally, it bends evenly without sharp bends. The structure described in U.S. Pat. No. 5,108,416 by Ryan, et al, when threaded over a guidewire bends unevenly, causing friction between the inner diameter of the catheter and the guidewire, making it impossible for this apparatus to be threaded to more tortuous arteries.

U.S. Pat. No. 5,158,548 by Lau and Hartigan describes an apparatus where a sheath-type device, similar to that described in U.S. Pat. No. 5,108,416, where the sheath or "holding cup" is attached to a central guidewire and the guidewire is advanced forward to expose the stent. This design has several drawbacks. First, it is necessary that the stent delivery catheter is advanced over a guidewire into position. The fact that the central lumen of the apparatus described is occupied by the wire described in the invention does not permit the placement of the stent delivery system over a guidewire. For safety reasons, most catheters, including balloon catheters and stent delivery catheters, are advanced over a guidewire. Catheters such as the one described in U.S. Pat. No. 5,158,548 by Lau, where a small guidewire portion is attached to a bulky sheath, often can cause perforations of the vasculature or can break plaque loose, causing severe complications, including death, when such happens in the coronary artery. Secondly, this design causes the distal portion of the catheter to be hard and bulky, and does not promote easy tracking of the catheter/balloon/stent into tortuous vasculature.

In addition, other methods and variations of these are present in the literature. In all of these cases, the inventors have failed to address the practical considerations due to the smallness and the complex and tortuous vasculature of the human arteries, especially the coronary arteries.

SUMMARY OF THE INVENTION

A catheter assembly for the delivery of a vascular stent into human arteries and veins is disclosed. The system disclosed in the present invention is an apparatus capable of deploying a vascular stent mounted on a catheter, either on a balloon catheter or on the distal portion of a catheter tube. In the case of a stent mounted on the balloon of a balloon catheter, the spring sheath is withdrawn and the balloon is inflated to deploy the stent to the inner wall of the vasculature. In the case of a self-expanding stent, the spring sheath is withdrawn, causing the stent to expand to the vessel wall. The apparatus is withdrawn after the stent has been deployed.

BRIEF DESCRIPTION OF THE DRAWINGS

FIG. 4A is an alternative embodiment showing the retainer on the proximal neck of the balloon in the run-in position.

FIG. 4B is the embodiment of FIG. 4A in the stent delivered position.

FIG. 5 is the view of FIG. 3 in the stent released position.

DETAILED DESCRIPTION OF THE PREFERRED EMBODIMENT

In an ideal stent-delivery system, the apparatus containing the stent should possess at least the following characteristics: (a) The stent should be secured so that it has no chance of sliding out of the apparatus; (b) the device should be flexible and able to track in three-dimensional vasculature over a guidewire; (c) the profile should be low so as to be able to cross pre- or post-dilated lesions; and (d) the device should have a smooth profile from the tip backwards so that its advancement into the lesion is easy.

Such a device is described in FIGS. 2–4B. Essentially, the stent is mounted on a low-profile balloon catheter. A thin-wall balloon made from polyester or nylon would provide a low-profile balloon. Inasmuch as stent deployment can require high pressure (16–22 atmospheres), this balloon should be able to withstand high pressures. If polyethylene is used as a balloon material, the profile is large and with the burst pressure being relatively less, it will not provide sufficient reliability in deploying the balloon.

Figure 1:
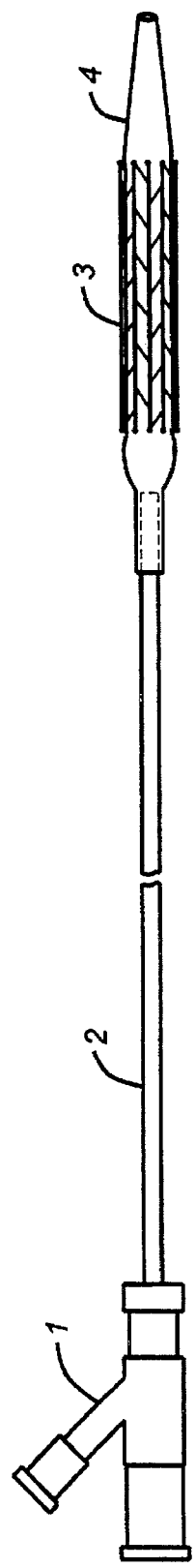
FIG. 1 is a sectional elevational view showing a stent mounted on a balloon, with the retainer removed for clarity.
Figure 2A:
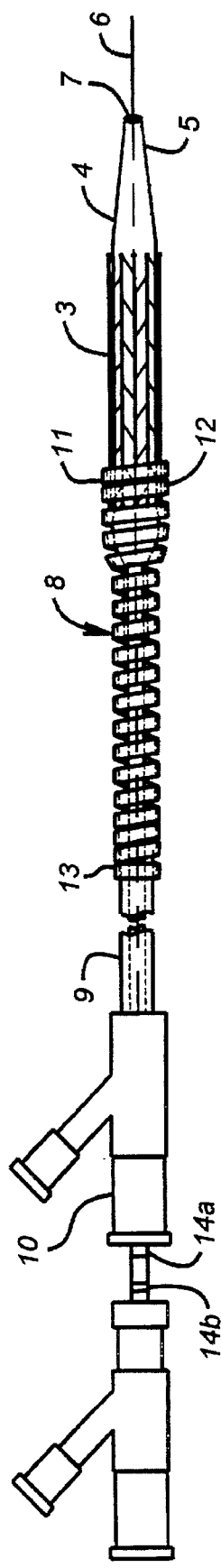
FIGS. 2A and 2B respectively show the stent held by the retainer for delivery and the stent in a delivered position.

In FIG. 2A, the metallic stent 3 is slid onto the folded balloon 4 of a balloon angioplasty catheter. The tip of the catheter 5 is conical or bullet-nosed to provide a smooth "shoulder"-free leading profile for the catheter. A guidewire 6 is advanced through the lumen 7. The stent can be self-expanding, in which case with a retractable spring 8 the stent can be actuated without a balloon.

FIG. 2A describes one of the variations of the proposed invention. A flexible spring 8 made of metallic material, such as stainless steel, platinum or rhenium, is attached on its proximal end to a polymer sheath 9 containing a "Y" adapter 10. On its distal end 11, the spring coil is positioned to cover at least a portion of the stent 3. The metallic coil is made of radiopaque material. If it is not, such as stainless steel in thin sections, the coil is either gold-plated or a band of radiopaque material is attached to the distal end of the coil. Also, it is possible that the distal 5–8 turns of the coil is made of platinum while the rest of the coil is made of stainless steel to reduce the cost of the device. The distal region of the coil 12 has coils that are more tightly packed (i.e., smaller pitch), while the final 3–5 turns 13 are essentially touching each other to facilitate fixation at its proximal end. In between, the pitch increases to provide flexibility. The 3–5 turns that overlap stent 3 are preferably closely packed.

The coil is preferably made from flat wire to improve the flexibility as well as to result in a lower profile, while round wire may also be used. In the preferred embodiment, the wire diameter is 0.002–0.004".

In a typical deployment of the stent, the sheath is located properly either covering the entire stent or a portion thereof. The apparatus is then advanced to the lesion location over a guidewire. The presence of radiopaque material enhances the radiopaque vision and allows the operator to locate the stent accurately at the lesion.

Figure 2B:
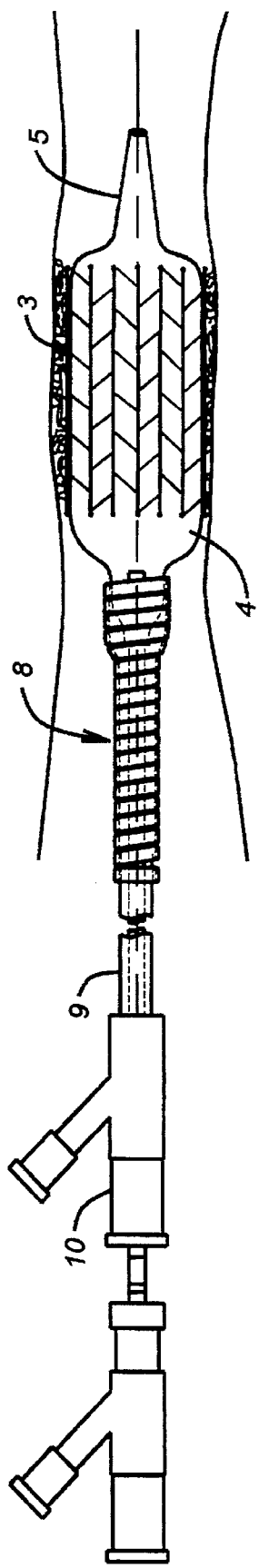

The sheath containing the spring wire coil assembly of FIG. 2 is then withdrawn from marked band 14a and marked band 14b and the balloon is inflated to deploy the stent. The balloon is deflated subsequently and the catheter is then withdrawn.

In an alternate method shown in FIG. 4A, the spring coil 20, again made from metallic material such as platinum, is placed over the stent, this time only partially, to sufficiently hold the stent in place. When the balloon is inflated to deploy the stent, the distally stretched strands of the spring will compress, releasing the stent from the grips of the final strands of the coil 22. Typically, 2–3 mm of overlap is sufficient to hold the stent in place. This method does not contain a proximal sheath and, therefore, further improves the flexibility of the catheter and enhances the trackability in three-dimensional vasculature.

In either of the designs, a soft, thin layer of glue can be used to glue the stent to the delivery catheter. When the balloon is inflated, the stent would expand from its glue joints, breaking the glue joints. Typically, starch, albumin, fibrin or chemical glues such as urethane, vinyl, etc., can be used so long as they are biocompatible and would not break into minute pieces when the balloon is inflated. A very thin solution of polyurethane is most ideal due to its flexibility after the glue sets and its biocompatibility properties. In an alternative embodiment, the stent 3 can be mounted on the balloon 4 with an adhesive that selectively holds it until the balloon 4 is expanded to release the grip of the adhesive, whereupon the stent 3 springs out to be set and the delivery system can be retracted upon balloon deflation.

Figure 3:
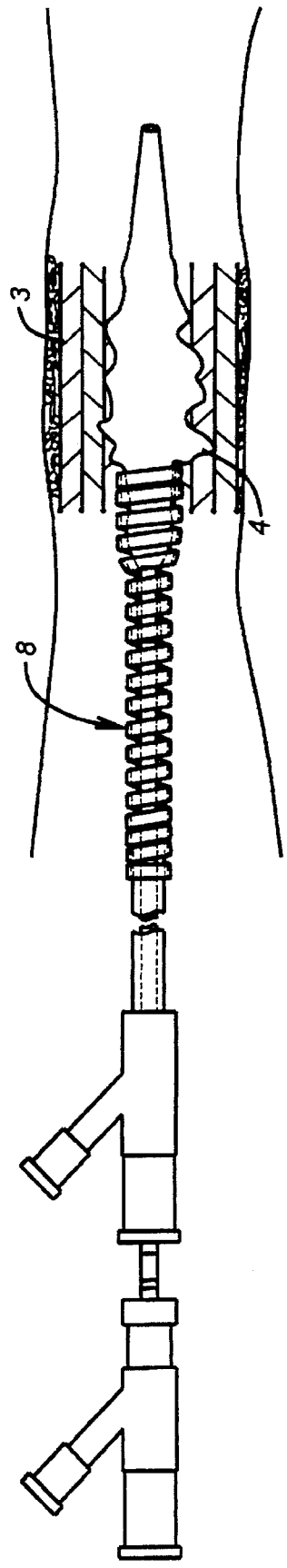
FIG. 3 is the view of FIG. 2 after delivery of the stent.

The use of a coiled wire retainer in the embodiments of FIGS. 2A and 3 gives a combined benefit of increasing the stent-retaining force while at the same time allowing greater flexibility to navigate in three dimensions through the vasculature. In prior designs using plastic retainers such as U.S. Pat. No. 5,108,416, the sheaths made of polymers such as polyurethane, even if provided at thicknesses as small as 0.003–0.004", are sufficiently stiff to prevent smooth bending to promote trackability. Sheaths of such plastics, even at 0.003–0.004", will kink especially when applied directly over the proximal and distal ends of a balloon. Using a coiled wire retainer with small-diameter or flat wire of about 0.002–0.004" allows retention of flexibility at key points at the proximal or distal (if used) end of the balloon. By increasing the pitch at the point of overlap, the flexibility at the key point of potential kink is increased without sacrificing the security of the grip. The retainer can be used both proximally and distally of the balloon, but the preferred embodiment is proximally only. While a coiled metal retainer is preferred, other variations of a wire structure can be used as a retainer without departing from the spirit of the invention. Such designs can involve a distally longitudinally split tube and expanded or perforated metal design or the like.

The foregoing disclosure and description of the invention are illustrative and explanatory thereof, and various changes in the size, shape and materials, as well as in the details of the illustrated construction, may be made without departing from the spirit of the invention.

I claim:

1. A stent-delivery apparatus, comprising:
an elongated support member;
an expanding member mounted to said elongated support member;
a stent mountable over said expanding member;
at least one retainer, said retainer initially overlapping said stent to releasably secure said stent until said expanding member is expanded, which triggers release of said stent by said retainer;
said retainer formed primarily of a metallic structure.

2. The apparatus of claim 1, wherein said retainer comprises a wire structure.

3. The apparatus of claim 2, wherein said wire has a coiled shape.

4. The apparatus of claim 3, wherein said wire is about 0.002–0.004" in its thickest section dimension.

5. The apparatus of claim 3, wherein:
said coiled shape has at least one pitch over its length.

6. The apparatus of claim 3, wherein:
said coil, having at least a portion thereof further comprising a radiopaque material.

7. The apparatus of claim 6, wherein:
said elongated support member comprises a balloon angioplasty catheter;
a expanding member comprises said balloon;
said catheter further comprises a smooth bullet-nosed end;
said balloon is capable of withstanding at least 16 atmospheres;
said stent is attached to said balloon by an adhesive.

8. The apparatus of claim 6, wherein:
said wire has a flat portion in cross-section.

9. The apparatus of claim 1, wherein:
said retainer overlaps said stent by about at least 2–3 mm.

10. The apparatus of claim 1, further comprising:
at least two retainers positioned over opposed ends of said stent.

11. A stent-delivery apparatus, comprising:
an elongated support member;
a stent mountable over said support member;
an expanding member on said support member to actuate said stent;
at least one retainer supported by said elongated support member, said retainer releasably securing said stent until said expanding member is actuated;
said retainer formed primarily of a metallic structure.

12. The apparatus of claim 11, wherein:
said retainer is retractable.

13. The apparatus of claim 12, wherein said retainer comprises a wire structure.

14. The apparatus of claim 13, wherein said wire is turned into coiled shape.

15. A vessel stent-delivery apparatus, comprising:
an elongated support member;
an expanding member mounted to said elongated support member;
a stent mountable over said expanding member, said stent being sufficiently structurally rigid to self support in the vessel as a result of actuation of said expanding member without chemical reaction;
an adhesive to selectively secure said stent to said expanding member; said adhesive releasing upon actuation of said expanding member so that said elongated support member can be removed only upon immediate contraction of said expanding member.

16. A stent-delivery apparatus, comprising:
an elongated support member;
an expanding member mounted to said elongated support member;
a stent mountable over said expanding member;
at least one retainer, said retainer initially overlapping said stent to releasably secure said stent until said expanding member is actuated;
said retainer formed primarily of a metallic structure having a coiled shape with at least one pitch over its length and wherein said pitch decreases in the area where the coil overlaps said stent.

17. The apparatus of claim 16, wherein:
said turns are in close contact at a point nearest said stent and are spaced apart moving away from said stent.

18. The apparatus of claim 17, wherein:
said turns are spaced about 1–2 mm apart at the point of overlap of said stent.

19. The apparatus of claim 18, wherein:
said retainer overlaps said stent by about at least 2–3 mm.

20. A stent-delivery apparatus, comprising:
an elongated support member;
an expanding member mounted to said elongated support member;
a stent mountable over said expanding member;
at least one retainer, said retainer initially overlapping said stent to releasably secure said stent until said expanding member is actuated;
said retainer formed primarily of a metallic structure having a coiled shape;
said coil having a proximal end secured to said expanding member adjacent a proximal end thereof.

21. The apparatus of claim 20, wherein:
said wire is approximately 0.002–0.004" in its largest section.

22. A stent-delivery apparatus, comprising:
an elongated support member;
an expanding member mounted to said elongated support member;
a stent mountable over said expanding member;

at least one retainer, said retainer initially overlapping said stent to releasably secure said stent until said expanding member is actuated;

said retainer formed primarily of a metallic structure having a coiled shape;

an outer sleeve mounted over a portion of said elongated support member;

said coil extending from said outer sleeve to said stent to overlap a portion thereof;

said outer sleeve movable longitudinally with respect to said elongated support member to facilitate release of said stent by retraction of said retainer.

23. The apparatus of claim 22, wherein said elongated support further comprises markings to give a visual feedback that the retainer has been retracted away from the stent due to movement of said outer sleeve.

* * * * *